United States Patent [19]

Higaki et al.

[11] Patent Number: 5,593,857
[45] Date of Patent: Jan. 14, 1997

[54] PRODUCTION OF HOMOGENEOUS TRUNCATED CNTF

[75] Inventors: Jeffrey N. Higaki, Mountain View; Edmund G. Tischer; Barbara Cordell, both of Palo Alto; Stewart A. Thompson, Mountain View, all of Calif.

[73] Assignee: Scios Inc., Mountain View, Calif.

[21] Appl. No.: 749,446

[22] Filed: Aug. 23, 1991

[51] Int. Cl.$^6$ .......................... C12N 15/12; C07K 14/47; C07K 14/475
[52] U.S. Cl. .......................... 435/69.1; 530/350; 530/399; 536/23.5
[58] Field of Search .......................... 530/350, 399, 530/412; 435/69.1, 252.3, 240.2, 252.33; 514/12; 536/23.5

[56] References Cited

U.S. PATENT DOCUMENTS

| | | | |
|---|---|---|---|
| 4,997,929 | 3/1991 | Collins et al. | 536/23.5 |
| 5,011,914 | 4/1991 | Collins et al. | 530/399 |
| 5,032,519 | 7/1991 | Paulson et al. | 435/172.3 |

FOREIGN PATENT DOCUMENTS

| | | |
|---|---|---|
| 0385060 | 9/1990 | European Pat. Off. |
| 0421059 | 4/1991 | European Pat. Off. |
| 9007341 | 7/1990 | WIPO |
| 9010647 | 9/1990 | WIPO |
| 9104316 | 4/1991 | WIPO |
| 9310233 | 5/1993 | WIPO |

OTHER PUBLICATIONS

Sabatini et al. *J. Cell Biol* 92:1–22 (1982).
Colley et al. *J. Biol Chem* 264(30):17619–17622 (1989).
Sofer et al. *Biotechniques* 1(4):198–203 (1983).
Suggs et al 1981. Use of Synthetic oligonucleotides as hybridization Probes. Proc Natl Acad Sci. 78:6613.
Manthrope et al. 1986. Purification of Adult Rat Sciatic Nerve Ciliary Neurotropic Brain Res 367:282.
Lin et al. 1989. Purification, Cloning and Expression of Ciliary Neurotropic Factor. Science 246:1023.
Collins et al. Jan. 11, 1991, Intelligenetics database R06557. New Sciatic Nerve ciliary neuro–.
Collins et al. Dec. 11, 1990. Intelligenetics Database RO6234. Purified sciatic nerve ciliary neuro–.
Collins et al. Jan. 11, 1991 Intelligenetics Database Q05801. New Sciatic nerve ciliary neurotropic.
Collins et al. Dec. 11, 1990. Intelligenetics Database Q05528. Purified Sciatic Nerve ciliary neurotropic.
Adler and Varon, *Brain Res.* (1980) 188:437–448.
Landa et al., *Dev. Biol.* (1980) 74:401–408.
Manthorpe et al., *J. Neurochem.* (1980) 34(1):69–75.
Manthorpe et al., *J. Neurochem.* (1982) 38:415–421.
Barbin et al., *J. Neurochem.* (1984) 43(5):1468–1478.
Manthorpe et al., *Brain Res.* (1986) 367:282–286.
Stockli et al., *Nature* (1989) 342:920–923.

*Primary Examiner*—Marianne P. Allen
*Attorney, Agent, or Firm*—Peter R. Shearer

[57] ABSTRACT

There are disclosed neurotrophic factors which are capable of being expressed as polypeptides lacking the microheterogeneity associated with a related native-sequence factor, CNTF. Also disclosed are DNA sequences encoding the neurotrophic factors and methods for expressing and recovering the factors as homogeneous polypeptides.

15 Claims, 4 Drawing Sheets

(MET) Ala Phe Thr Glu His Ser Pro Leu Thr Pro His Arg Arg Asp Leu Cys Ser
Arg Ser Ile Trp Leu Ala Arg Lys Ile Arg Ser Asp Leu Thr Ala Leu Thr Glu
Ser Tyr Val Lys His Gln Gly Leu Asn Lys Asn Ile Asn Leu Asp Ser Ala Asp
Gly MET Pro Val Ala Ser Thr Asp Gln Trp Ser Glu Leu Thr Glu Ala Glu Arg
Leu Gln Glu Asn Leu Gln Ala Tyr Arg Thr Phe His Val Leu Leu Ala Arg Leu
Leu Glu Asp Gln Gln Val His Phe Thr Pro Thr Glu Gly Asp Phe His Gln Ala
Ile His Thr Leu Leu Leu Gln Val Ala Ala Phe Ala Tyr Gln Ile Glu Glu Leu
MET Ile Leu Leu Glu Tyr Lys Ile Pro Arg Asn Glu Ala Asp Gly MET Pro Ile
Asn Val Gly Asp Gly Gly Leu Phe Glu Lys Lys Leu Trp Gly Leu Lys Val Leu
Gln Glu Leu Ser Gln Trp Thr Val Arg Ser Ile His Asp Leu Arg Phe Ile Ser
Ser His Gln Thr Gly Ile Pro Ala Arg Gly Ser His

FIG. 1

```
ATG GCT TTC ACA GAG CAT TCA CCG ACC CCT CAC CGT CGG GAC CTC TGT AGC
                                    27                                  54
CGC TCT ATC TGG CTA GCA AGG AAG ATT CGT TCA GAC CTG ACT GCT CTT ACG GAA
                                    81                                 108
TCC TAT GTG AAG CAT CAG GGC CTG AAC AAG AAC ATC AAC CTG GAC TCT GCG GAT
                                   135                                 162
GGG ATG CCA GTG GCA AGC ACT GAT CAG TGG AGT GAG CTG ACC GAG GCA GAG CGA
                                   189                                 216
CTC CAA GAG AAC CTT CAA GCT TAT CGT ACC TTC CAT GTT TTG GCC AGG CTC
                                   243                                 270
TTA GAA GAC CAG CAG GTG CAT TTT CTC CAA ACC GAA GGT GAC TTC CAT CAA GCT
                                   297                                 324
ATA CAT ACC CTT CTC CAA GTC GCT GCC TTT GCA TAC CAG ATA GAG GAG TTA
                                   351                                 378
ATG ATA CTC CTG GAA TAC AAG ATC CGC AAT GAG GCT GAT GGG ATG CCT ATT
                                   405                                 432
AAT GTT GGA GAT GGT GGT CTC TTT GAG AAG AAG CTG TGG GGC CTA AAG GTG CTG
                                   459                                 486
CAG GAG CTT TCA CAG TGG ACA GTA AGG TCC ATC CAT GAC CTT CGT TTC ATT TCT
                                   513                                 540
TCT CAT CAG ACT GGG ATC CCA GCA CGT GGG AGC CAT TAG
                                   567
```

PRODUCTION OF HOMOGENEOUS TRUNCATED CNTF

This invention was made with government support under Grant No. 1-R43-AG09705-01 awarded by the National Institute of Health. The government retains certain rights in this invention.

FIELD OF THE INVENTION

This invention relates to the field of neurotrophic factors. In particular, the invention relates to the recombinant production and recovery of novel neurotrophic factors which lack microheterogeneity that is associated with the recombinant production of a related native-sequence factor.

BACKGROUND OF THE INVENTION

Neurotrophic factors are proteins which, inter alia, promote the survival of neurons and stimulate neurite growth (axonal and dendritic processes) and the synthesis of function-related neuronal enzymes. A number of factors have been isolated which have neurotrophic activities, including nerve growth factor (NGF) and fibroblast growth factors.

Beginning in the late 1970's, "ciliary neurotrophic factors" (CNTFs) were described and preliminarily characterized. CNTF was originally identified as a factor which is specifically required for the survival of one population of neurons, the chick embryo cholinergic parasympathetic motor neurons of the ciliary ganglion. CNTF is also able to support certain NGF-responsive neurons. Chick eye CNTF was shown to be a 20.4 kD protein with an isoelectric point of 5.0 which supported the survival not only of ciliary ganglion neurons but also cultured avian and mammalian sensory neurons and avian sympathetic neurons (Adler and Varon, *Brain Res.* (1980) 188:437–448; Landa et al., *Dev. Biol.* (1980) 74:401–408; Manthorpe et al., *J. Neurochem* (1980) 34:69–75; Barbin et al., *J. Neurochem.* (1984) 43:1468–1478; Manthorpe et al., *J. Neurochem.* (1982) 38:225–242).

Partially purified CNTF was isolated from rat sciatic nerves and shown to have a specific activity of $2\times10^7$ trophic units (TU) per mg. (Manthorpe et al., *Brain Res.* (1986) 367:282–286). Homogeneous CNTF was subsequently obtained from rat sciatic nerves (PCT Application No. PCT/US90/01390). The obtainment of sequenceably pure CNTF made it possible to isolate DNA sequences encoding mammalian CNTFs, including rat, rabbit and human CNTF (Stockli et al., *Nature* (1989) 342:920–923; European Patent Application No. 0 385 060; Lam et al., *Gene* in press) and to deduce their complete amino acid sequences. Human CNTF has been determined to be a protein 200 amino acids in length.

SUMMARY OF THE INVENTION

CNTF has been produced by us recombinantly at high levels in bacterial hosts. After expressing and recovering CNTF, however, it has been observed that the recovered material exhibits a substantial amount of microheterogeneity. This microheterogeneity, which is apparent when the product is analyzed by ion-exchange HPLC and other chromatographic columns such as MonoQ FPLC, is believed to result from post-translational modifications at both the C-terminus and the N-terminus of the molecule. In particular, the C-terminal end of the molecule is believed to be subject to enzymatic degradation within the host cell. Heterogeneity at the N-terminus may be due to N-terminal acetylation of some of the expressed CNTF.

Because of the microheterogeneity observed with recombinantly produced CNTF, its commercial production as a therapeutic product, e.g. for use in the treatment of Parkinsonism, amyotrophic lateral sclerosis, Alzheimer's disease or nerve death caused by trauma, is rendered considerably more difficult. Lack of homogeneity makes it difficult to obtain a consistent manufacturing process. Moreover, the rigorous analytical characterization and characterization of efficacy which are generally required of pharmaceutical products are made more difficult.

It would be highly desirable to produce a product which has biological activities the same as or similar to CNTF, but which lacks the microheterogeneity problems associated with the recombinant production of CNTF.

The present invention provides a novel neurotrophic factor having essentially the same activity as CNTF, but lacking the microheterogeneity associated with recombinantly produced CNTF. The invention is based, in part, on our discovery that deletion of an appropriate portion of the C-terminal end of the human CNTF molecule results in a molecule which can be produced recombinantly without the enzymatic degradation observed with recombinantly produced CNTF, yet retains essentially the same neurotrophic activity as CNTF. In particular, we have found that deletion of at least 8 C-terminal amino acids from CNTF results in a product that is homogeneous by recombinant production. As many as 22 C-terminal amino acids can be deleted while maintaining homogeneity and retaining essentially the same biological activity as CNTF. By "essentially the same" is meant that the factor exhibits at least about 50% of the activity of CNTF in the choline acetyltransferase assay. A somewhat less preferred embodiment of the invention is based on our discovery that up to 20 N-terminal amino acids can be deleted, in combination with the aforementioned C-terminal deletions, to yield a factor which lacks microheterogeneity and which has useful neurotrophic activity, i.e. at least about 10% of the activity of CNTF in the choline acetyltransferase assay. At this level of activity, the factor is sufficiently potent to be useful as a neurotrophic factor.

Figure 1:
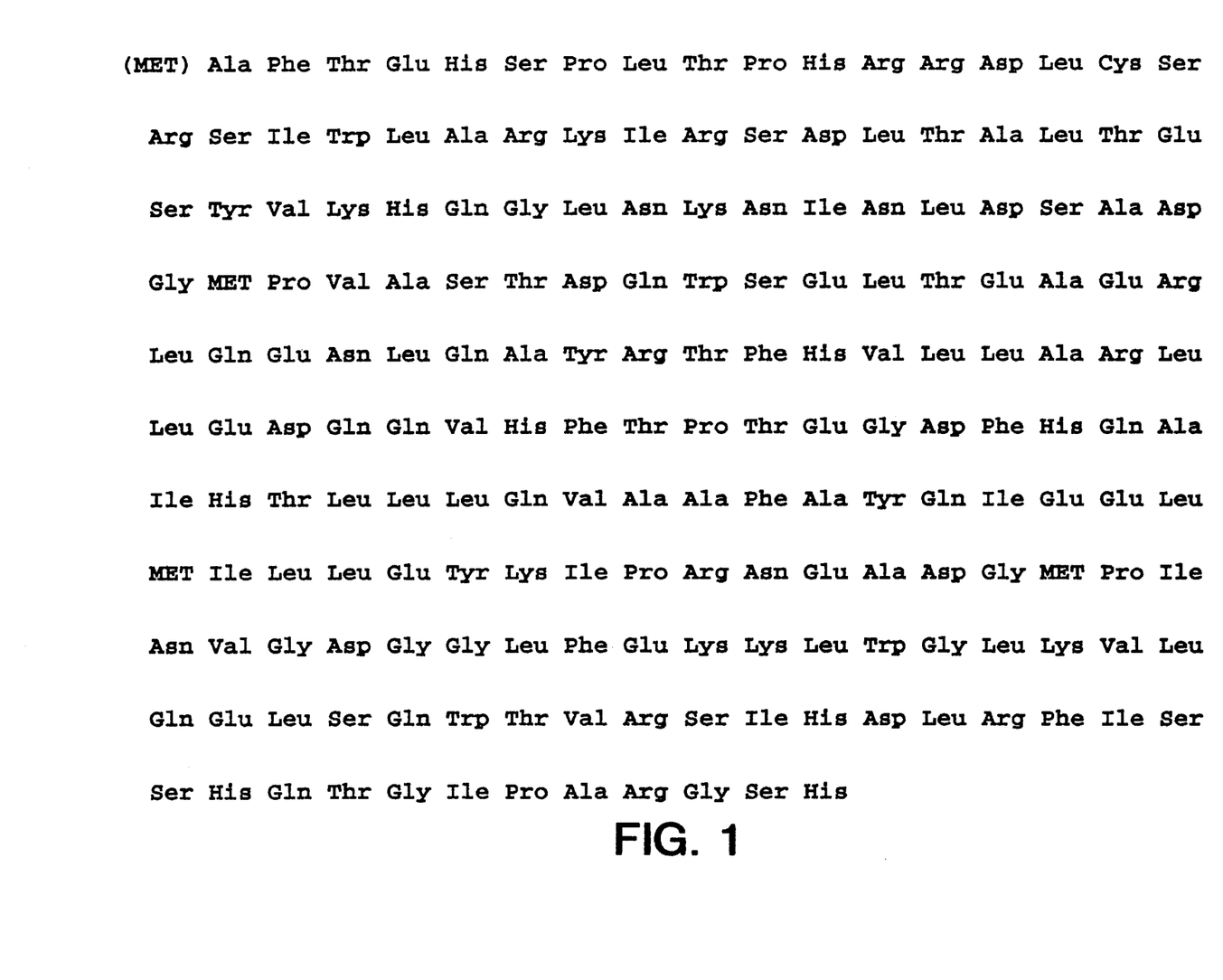
FIG. 1 represents the amino acid sequence of amino acids No. 1 to 192 of neurotrophic factor of the invention.

The neurotrophic factor of the invention comprises a polypeptide having the amino acid sequence of residues m through n of FIG. 1 [Seq. I.D. No. 001] wherein m is an integer from 1 to 21 and n is an integer between 172 and 192. Preferably, n is an integer between 178 and 192. Most preferably n is an integer between 180 and 192.

The present invention also provides a recombinant DNA sequence encoding the above-identified neurotrophic factor, as well as methods for the recombinant production of the factor.

In another embodiment of the invention, there is provided a method for producing isolated homogeneous neurotrophic factor, which comprises:

(a) expressing a DNA sequence encoding the above-identified neurotrophic factor in a bacterial host cell;

(b) lysing the host cell and applying the lysate to an immobilized material capable of binding the neurotrophic factor by hydrophobic interaction;

(c) eluting a fraction containing the neurotrophic factor from the immobilized material and contacting said fraction with an immobilized metal ion capable of forming a chelate complex with the neurotrophic factor;

(d) eluting a fraction containing the neurotrophic factor from the immobilized metal ion and applying said fraction to a reverse phase HPLC column; and (e) eluting from the reverse phase HPLC column a fraction containing isolated homogeneous neurotrophic factor.

DESCRIPTION OF THE DRAWINGS

FIG. 3 is a schematic representation of a fragment of the expression vector pSP18 containing the DNA sequence for full-length CNTF.

FIG. 4 is a schematic representation of expression vector pSP18 containing an insert encoding full-length CNTF.

DETAILED DESCRIPTION OF THE INVENTION

As previously indicated, the invention is based on our discovery that deletion of an appropriate portion of the C-terminus of full-length (200 amino acids) CNTF results in a molecule which retains essentially the same biological activity but, unlike CNTF, is capable of being produced recombinantly without the heterogeneity associated with recombinant CNTF. Additionally, up to 20 amino acids can be deleted from the N-terminus of CNTF, in combination with the aforementioned C-terminal deletion, without an unacceptable loss of activity.

The neurotrophic factor of the invention is produced recombinantly by the expression, in a bacterial or other suitable host, of a DNA sequence encoding the polypeptide. The DNA sequence encoding the neurotrophic factor of the invention can be produced by any number of known techniques. For example, a complete sequence of codons, which may be selected for maximal expression in the particular host cell being employed, can be assembled from overlapping synthetic oligonucleotides using known techniques.

As previously indicated, the obtainment of sequenceably pure CNTF has allowed the isolation of native DNA sequences encoding CNTF of several species. A cDNA sequence encoding human CNTF is disclosed, for example, in FIG. 12 of European Patent Publication No. 0 385 060. The DNA sequence employed to express the neurotrophic factor of the present invention can be derived from the native CNTF sequence using the technique of polymerase chain reaction (PCR) to amplify any desired portion(s) of the CNTF sequence one wishes to include in the neurotrophic factor. PCR is a technique which is described in detail in U.S. Pat. Nos. 4,683,202 and 4,683,195, the disclosures of which are incorporated herein by reference. The procedure allows the amplification of a desired nucleotide sequence, even if the bulk of the sequence is not known, provided one is able to provide oligonucleotide primers that will hybridize to either end of the sequence that it is desired to amplify. After isolating and sequencing a cloned cDNA encoding human CNTF, we prepared DNA sequences encoding the neurotrophic factors of the present invention by the following general procedure which is described with reference to FIG. 3. FIG. 3 is a schematic representation of a fragment of the expression vector pSP18 containing the DNA sequence for full-length CNTF on an NdeI to HindIII segment. This vector, which can be employed as a starting material to prepare expression vectors encoding the neurotrophic factors of the invention, was deposited with the American Type Culture Collection, Rockville, Md., on Aug. 23, 1991 with Accession No. ATCC 75071. In order to prepare DNA encoding the C-terminal portion of the neurotrophic factor of the invention, two synthetic oligonucleotide primers were prepared, one of which was complementary to a portion of the CNTF sequence containing the mid-sequence HindIII site and one of which was complementary to a portion of the CNTF DNA encoding the desired C-terminus. The primer corresponding to the desired C-terminus also contained a HindIII sequence at its 3' end. One of the primers corresponded to the sense strand and the other to the anti-sense strand.

The portion of the CNTF sequence lying between the mid-sequence HindIII site and the desired 3' terminus was then reproduced and amplified by: hybridizing the primers to single-stranded pSP18 DNA; priming synthesis of DNA at approximately 72° C. in the presence of dNTPs and the *Thermus aquaticus* (Taq) polymerase; separating the synthesized strands from the CNTF template by raising the temperature to approximately 94° C.; and then using the synthesized strands as templates for the synthesis of new strands corresponding to the desired sequence through a series of hybridizations, followed by Taq-catalyzed synthesis of complementary strands and separation of template-strands from synthesized-strands. The DNA sequence encoding the desired neurotrophic factor was then isolated on a polyacrylamide gel and cut with HindIII. The resulting DNA sequence encoded the C-terminal portion of the neurotrophic factor of the invention on a HindIII-HindIII fragment. This fragment was inserted into HindIII-cut pSP18 to replace the full-length 3' end of the CNTF coding sequence, thereby creating an expression vector for the neurotrophic factor of the invention.

In order to prepare a neurotrophic factor of the invention in which the N-terminal amino acid is at a position other than amino acid No. 1 of FIG. 1, the DNA sequence encoding the N-terminal portion can be prepared, using PCR in a manner similar to that described above to amplify the desired N-terminal portion of the CNTF sequence. Referring to FIG. 3, the first oligonucleotide primer used for this purpose corresponds to a portion of the CNTF sequence beginning with an NdeI site, followed a translation initiation codon (ATG) and then the codon for the desired N-terminal amino acid. The other primer corresponds to a portion of the CNTF sequence containing the BclI restriction site. Amplification by PCR using these primers results in a fragment which can be cut with NdeI and BclI to yield a DNA sequence encoding the N-terminal portion of the neurotrophic factor of the invention on an NdeI-BclI fragment. This fragment can be ligated into pSP18 containing the previously described insert which has the 3' coding region for the neurotrophic factor of the invention, and which has been cut with NdeI and BclI, to provide an expression vector for the neurotrophic factor of the invention.

Preferred DNA sequences encoding the neurotrophic factor of the invention are represented in FIG. 2. Thus, for example, where the neurotrophic factor consists of the amino acid sequence of amino acids 1–180 of FIG. 1, the preferred DNA sequence is represented by the sequence of nucleotides no. 1–540 in FIG. 2. When the neurotrophic factor consists of the amino acid sequence of amino acids No. 1–178 of FIG. 1, then the preferred DNA sequence is represented by the sequence of nucleotides 1–534 of FIG. 2. When the neurotrophic factor consists of the amino acid sequence of amino acids No. 1–190 of FIG. 1, then the preferred DNA sequence is represented by the sequence of nucleotides No. 1–570 in FIG. 2. When the neurotrophic factor consists of the amino acid sequence of amino acids No. 21–180 of FIG. 1, then the preferred DNA sequence is represented by the sequence of nucleotides No. 63–540 of FIG. 2. The isolated DNA sequences encoding the neurotrophic factor of the invention may also contain additional nucleotides at the 5' or 3' end to facilitate insertion into appropriate vectors or to facilitate expression. For example, they may contain "start" or "stop" codons or endonuclease restriction sites to facilitate ligation into vectors. When an ATG start codon is inserted at the 5' end, it will be understood that translation of the DNA sequence will produce an N-terminal methionine, however, this residue will normally be processed off the polypeptide within the host cell.

Figure 4:
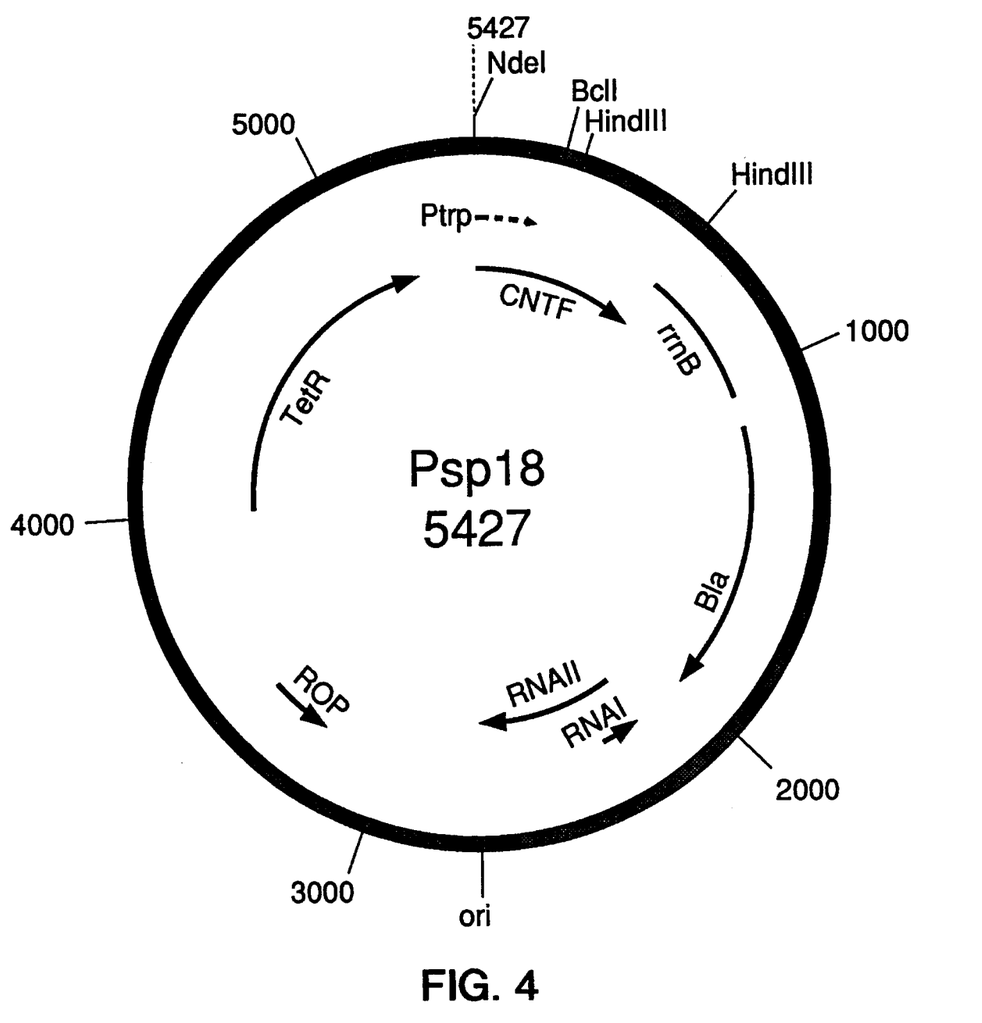

The DNA sequence encoding the neurotrophic factor of the invention is inserted into a suitable expression vector which is replicable in the host cell and which contains appropriate regulatory elements, such as a promoter and operator, for directing and controlling expression of the factor. A suitable expression vector is pSP18, illustrated schematically in FIG. 4. This vector contains a Trp promoter, genes for tetracycline and ampicillin resistance, and a bacterial origin of replication. The vector contains an insert encoding CNTF on an NdeI-HindIII segment. As previously described the 3' end of the CNTF gene and, if desired, the 5' end, can be deleted and replaced with the corresponding coding regions of the neurotrophic factor of the invention.

The expression vector containing the coding sequence for the neurotrophic factor of the invention is used to transform a suitable host cell such as E. coli W3110. The host cell is grown up under appropriate conditions and the neurotrophic factor is expressed in a conventional manner.

In one embodiment of the invention there is provided an efficient, high yield process for recovering the expressed neurotrophic factor of the invention. Following expression, the host cells are separated from the growth medium, for example by centrifugation or filtration, and resuspended in an aqueous buffer, preferably at a pH of greater than 7.5. The neurotrophic factor is released by lysis of the bacterial host cell. Any of the known chemical, enzymatic or mechanical means may be employed such as sonication, disruption by Manton Gaulin homogenizer or by the use of lysozyme.

After removal of cell debris, the aqueous medium containing the neurotrophic factor is adjusted to a final concentration of 2M NaCl and then applied to an immobilized material capable of binding the neurotrophic factor through hydrophobic interaction. The immobilized material can be in the form of a packed column such as a phenyl-sepharose column. Such columns and packing materials are commercially available, for example, from Pharmacia and conditions for their use are known and available from the manufacturers. A suitable column for use in this step is the phenyl-sepharose CL-4B column (Pharmacia), although other hydrophobic interaction columns would be suitable. The column is then eluted using a decreasing salt gradient and a fraction containing the neurotrophic factor is isolated. Fractions containing the neurotrophic factor can be identified by assaying for neurotrophic activity using the choline acetyl transferase assay described in detail below. We have found that the majority of the neurotrophic factor elutes from the phenyl-sepharose column between 1.5M and 1.0M NaCl in 20 mM Tris, pH 8.0. Alternatively, the aqueous medium containing the neurotrophic factor can be contacted with a membrane activated with hydrophobic groups, e.g. phenyl groups, and the neurotrophic factor then eluted batchwise from the membrane.

Following separation by hydrophobic interaction, the neurotrophic factor is further purified by contacting it with an immobilized metal ion capable of forming a chelate complex with the neurotrophic factor. Preferably, the metal ion is immobilized in a packed column. Preferred columns are sepharose columns containing immobilized divalent metal ions such as $Cu^{+2}$, $Zn^{+2}$, $Ni^{+2}$, $Mn^{+2}$, $Mg^{+2}$ or $Ca^{+2}$. Such columns are commercially available, for example, from Pharmacia. The fraction is eluted from the column with an increasing imidazole gradient. The majority of the neurotrophic factor elutes at about 10 mM imidazole on a $Zn^{+2}$ chelating column and at 25 mM imidazole on a $Cu^{+2}$ chelating column. Alternatively, the neurotrophic factor can be contacted with a divalent metal ion immobilized on a membrane and subsequently eluted from the membrane in a batchwise manner.

If desired, the phenyl-sepharose step in the above-described purification procedure can be replaced by chromatography on a DEAE-sepharose fast flow column. Purification achieved by this column step is comparable to that achieved on phenyl-sepharose.

Any remaining minor protein contaminants can be removed by reverse phase HPLC. The neurotrophic factor of the invention elutes as a single peak from the reverse phase HPLC column. The eluted neurotrophic factor appears as a single band on an SDS-polyacrylamide gel. Mass spectrometry, ion-exchange HPLC and tryptic mapping confirm that the neurotrophic factor is recovered as a single molecular species with a homogeneous C-terminus.

If desired, following the metal chelating chromatography step, the sample can be further purified by size-exclusion chromatography using, for example a Superose 12 (HR10/30) FPLC column (Pharmacia), equilibrated with 20 mM Tris, pH 8.0 containing 0.3M NaCl. All of the chromatography steps described in the purification process should be carried out between 4° C. and 25° C., since the neurotrophic factor is stable in this range.

As can be seen in Table 1, Example 5, infra., some forms of the neurotrophic factor of the invention may be expressed in a recombinant host in insoluble form. The insoluble forms of the neurotrophic factors can be solubilized in a chaotropic agent such as 4–8M urea or 4–8M guanidine HCl. The chaotropic agent is then removed, for example by dialysis, and the neurotrophic factor is allowed to refold into its native conformation, in which it is soluble and biologically active. The use of urea or guanidine HCl to solubilize and refold proteins that are expressed recombinantly in insoluble form is generally quite well known in the art. Once the neurotrophic factor has been solubilized and refolded, it can be purified using the steps described above.

The recovered, homogeneous neurotrophic factor is useful in the treatment of conditions which involve the death of nerve cells or in maintaining the survival of such cells in culture. Such conditions include neurodegenerative diseases, e.g. Parkinsonism, amyotrophic lateral sclerosis, and Alzheimer's disease, as well as nerve death caused by traumatic injury, ischemia resulting from stroke or the natural aging process. The neurotrophic factor can be formulated with conventional pharmaceutically acceptable carrier vehicles and excipients suitable for delivery of the factor to the site of nerve damage. For example, the factor may be formulated as an injectable solution or it may be incorporated into a matrix suitable for forming an implant, e.g. a collagen matrix, for delivery at dosages ranging from 0.01 µg to 1 mg/kg body weight.

The following examples are presented for the purpose of further illustrating the practice of the invention and are not to be construed as limiting the invention in any manner. In the examples, the neurotrophic factors will be identified using the nomenclature NF(x–y), wherein x and y designate the amino acid positions in FIG. 1. For example, NF(1–178) designates the polypeptide having the amino acid sequence of positions 1–178 of FIG. 1.

The neurotrophic factors of the invention were assayed for activity in the choline acetyltransferase assay, which was modified from the procedure of Fonnum, F., *J. Neurochem.* (1975) 19:407-400. The assay measures the ability of the test compound to stimulate production of choline acetyltransferase by LAN-2 human neuroblastoma cells (Seeger et al., *Cancer Res.* (1977) 37:1364–1371). Essentially identical results were obtained using primary cultures of chick ciliary ganglion neurons.

Cells are seeded in 96-well microtiter plates at 5500 cells/well/100 µl growth media (L15 media+15% heat-inactivated fetal bovine serum plus penicillin and streptomycin and L-glutamine supplement). The microtiter plates are incubated for 2 hours at 37° C. prior to adding samples of neurotrophic factors.

Four-fold serial dilutions of the neurotrophic factor samples are prepared in phosphate buffered saline (PBS) with added $Ca^{+2}$, $Mg^{+2}$ and 0.2% gelatin. The samples are then adjusted by diluting to an initial concentration of 100 ng/ml. The 100 ng/ml of neurotrophic factor is serially diluted by transferring 50 µl of the diluted sample+150 µl PBS+$Ca^{+2}$+$Mg^{+2}$+0.2% gelatin.

After the 2-hour incubation of the microtiter plates containing the LAN-2 cells, there were added 10 µl/well of the serial dilutions in triplicate to the plates. The plates were then incubated for 48 hours at 37° C. under 10% $CO_2$.

In order to determine the ability of the neurotrophic factor to stimulate choline acetyltransferase, the following reaction, which is catalyzed by choline acetyltransferase, was employed:

Following incubation of cells with neurotrophic factor, the media was removed from the wells and 60 µl of the following reaction mixture was added to each well:
A. 150 mM NaCl 10 mM sodium phosphate pH 7.4

10 mM EDTA 1.5 mM choline chloride 0.15% bovine albumin 0.1% NP-40

B. 0.1 mM eserine

C. 0.1 mM Acetyl-CoA

D. 4.4 µCi/ml [$^3$H]Acetyl-CoA

After incubating for 2 hours at 37° C., 50 µl was removed from each well and pipetted into 7 ml (14×53 mm) scintillation vials containing 1.5 ml 10 mM sodium phosphate, pH 7.4. [$^3$H]Acetylcholine was extracted into an organic scintillant using tetraphenylboron by adding 1.5 ml of scintillation fluid consisting of a mixture of 800 ml Liquifluor and 200 ml of a 5 mg/ml solution of sodium tetraphenylboron in acetonitrile. The vials were rocked gently for one minute, the layers allowed to separate for at least ten minutes and the vials were placed in a scintillation counter.

The data from the scintillation counter was plotted as counts per minute [$^3$H]Acetylcholine versus ng/ml neurotrophic factor. The $ED_{50}$ was determined as the concentration required to give half-maximal [$^3$H]Acetylcholine production. Activity of the neurotrophic factors of the invention is expressed as the ratio of the $ED_{50}$ of the neurotrophic factor to that of CNTF×100%.

Example 1

Preparation of DNA Encoding Neurotrophic Factor NF(1–180)

In order to obtain a DNA sequence encoding the neurotrophic factor NF(1–180), a portion of the DNA sequence encoding amino acids No. 76 to 180 of full-length CNTF was amplified using polymerase chain reaction (PCR). The CNTF DNA sequence was amplified from a bacterial expression vector, plasmid pSP18 (FIG. 4), which contains the full-length CNTF sequence under the control of a Trp promoter. The PCR reaction was carried out using a synthetic 34-mer oligonucleotide primer corresponding to the sense strand for amino acids 76 to 87 of CNTF; and a synthetic 38-mer oligonucleotide primer corresponding to the anti-sense strand for amino acids 172 to 180 followed by a TAG stop codon and a HindIII restriction site. The 5' sense oligonucleotide had the sequence 5'-CCTTCAAGCT-TATCGTACCTTCCATGTTTTGTTG [Seq. I.D. No. 003]. The 3' anti-sense oligonucleotide had the sequence 5'-CCAAGCTTCTAAGAAATGAAACGAAGGT-CATGGATGGA [Seq. I.D. No. 004]. PCR was performed using these two oligonucleotide primers in the presence of 25 ng of CNTF expression vector pSP18, dNTPs, and *Thermus aquaticus* (Taq) polymerase. The PCR reaction was carried out for 30 cycles using the following program: denature one minute at 94° C. to form single stranded DNA; anneal two minutes at 55° C.; and perform second strand synthesis at 72° C. for 3 minutes. After PCR, the reaction was phenol:chloroform extracted and ethanol precipitated. The DNA was then digested with the restriction endonuclease HindIII and run on a 6% polyacrylamide gel. The DNA band corresponding to the correct size was cut from the gel and electroeluted overnight.

Example 2

Expression of Neurotrophic Factor NF(1–180)

Following ethanol precipitation, the DNA fragment obtained in Example 1 was ligated into pSP18 which had been cut with HindIII. The resulting expression vector, containing the complete coding sequence for NF(1–180) under the control of a Trp promoter, was transfected into a host strain, *E. coli* W3110. Colonies from the transfection were screened for expression of NF(1–180) by taking colony lysates and analyzing them directly on SDS polyacrylamide gels. Positives were detected by a new protein band migrating slightly faster than wild type CNTF.

A colony expressing NF(1–180) was grown in complete M9 media to an O.D. 600 of 0.4 at 30° C. Induction of CNTF was done by the addition of 30 µg/ml of 3β-indoleacrylic acid and grown overnight at 30° C. Crude protein prepared for assays was made by the following freeze/thaw protocol: one ml of cells of an induced overnight culture was spun down, then resuspended in 250 µl 100 mM Tris pH 7.5, 1 mM EDTA, 250 µg/ml lysozyme, and 20 µg/ml DNase. The mixture was allowed to sit on ice 30 minutes, followed by three freeze/thaw steps. The sample was brought to 10 mM $MgCl_2$ and placed on ice 30 minutes more. The sample was spun 10 minutes at 4° C., after which the supernatant was assayed for activity in the choline acetyltransferase assay.

Example 3

Purification of Neurotrophic Factor NF(1–180)

Two liters of E. coli W3110 transfected as described in Example 2 were grown overnight (16 hrs) in M9 media containing 100 µg/ml tetracycline. The cells were harvested by centrifugation to yield 30 g of cell paste. Cells were resuspended in 250 ml of 20 mM Tris, pH 8.0. Cells were lysed by sonicating on ice for 5 min. For larger scale preparations, lysozyme can be added to facilitate cell lysis or disruption can be accomplished using a Manton Gaulin homogenizer.

The cell lysate was centrifuged (9,000 rpm, GSA rotor, 20 min) and the supernatant was recovered. NaCl was added to a final concentration of 2M. The supernatant was then loaded onto a 20 ml column of phenyl-sepharose CL-4B (Pharmacia) which had previously been equilibrated with 20 mM Tris, pH 8.0, 2M NaCl. The loaded column was washed with starting buffer until a baseline absorbance (280 nm) was reached (<0.1 OD units). The column was eluted with a stepwise, decreasing salt gradient, as follows:

a) 100 ml 20 mM Tris, pH 8.0, 1.5M NaCl
b) 100 ml 20 mM Tris, pH 8.0, 1.0M NaCl
c) 100 ml 20 mM Tris, pH 8.0, 0.5M NaCl
d) 100 ml 20 mM Tris, pH 8.0, 0.2M NaCl
e) 100 ml 20 mM Tris, pH 8.0

The majority of the active protein eluted in the 1.5 and 1.0M NaCl fractions. These fractions were collected and diluted with 20 mM Tris, pH 8.0 to adjust the NaCl concentration to 0.5M NaCl.

The combined active fractions from the phenyl-sepharose column were loaded onto a 15 ml chelating sepharose 6B column (Pharmacia) which had previously been charged with $Zn^{+2}$ and equilibrated with 20 mM Tris, pH 8.0, 0.5M NaCl. The column was washed with starting buffer until the absorbance (280 nm) reached baseline (<0.1 OD units). The column was eluted with a stepwise increasing gradient of imidazole as follows:

a) 100 ml 20 mM Tris, pH 8.0, 2.5 mM imidazole
b) 100 ml 20 mM Tris, pH 8.0, 5.0 mM imidazole
c) 100 ml 20 mM Tris, pH 8.0, 10.0 mM imidazole
d) 100 ml 20 mM Tris, pH 8.0, 20.0 mM imidazole
e) 100 ml 20 mM Tris, pH 8.0, 40.0 mM imidazole
f) 100 ml 20 mM Tris, pH 8.0, 100.0 mM imidazole The majority of active protein eluted in the 10 mM imidazole fraction, although a significant amount eluted in the 20 mM fraction as well. These fractions were pooled separately. The final yield was about 35 mg of protein. The sample was then concentrated by filtration with a YM10 membrane (Amicon).

The protein was then injected onto a C18 reverse-phase HPLC column (Vydac) and eluted with an increasing acetonitrile gradient. The NF(1–180) eluted at 55–60% acetonitrile.

Example 4

Preparation of DNA Encoding NF(21–180)

A DNA sequence coding for human CNTF(21–200), was obtained by PCR using, as a template, the pSP18 vector containing the insert encoding full-length CNTF. The 5' sense oligonucleotide, 5'-ACGTAAAAAGGGTATCA-CATATGATCTGGCTAGCAAGGAAGATTCGT [Seq. I.D. No. 005] is a 47-mer which contains an NdeI restriction site followed by an ATG start codon and nucleotides encoding amino acids 21–28 of FIG. 1. The 3' antisense oligonucleotide, 5'-GGTTCTCTTGGAGTCGCTCTGCCTCGG [Seq. I.D. No. 006] is a 27-mer which ranges from amino acids No. 68 to 77 of FIG. 1. Using these two oligonucleotide primers, the sequence lying between the codons for amino acids No. 21 and 77 were amplified by PCR as described above in Example 1. Upon digestion with NdeI and BclI and gel isolation, the resultant DNA sequence encoded amino acids No. 21–62, preceded by a Met start codon, on an NdeI-BclI fragment. This fragment was ligated into pSP18, which had been cut with NdeI and BclI, to yield an expression vector for CNTF(21–200). To obtain NF(21–180), the HindIII fragment from NF(1–180) was gel purified and ligated back into HindIII-cut CNTF(21–200) and screened for positives. The NF(21–180) is expressed and purified in the same manner described above for NF(1–180).

Example 5

Analysis of Activity and Expression Characteristics

Several of the neurotrophic factors of the invention were prepared in the manner described above and were tested for neurotrophic activity by the procedure previously outlined. As controls, a number of polypeptides consisting of the amino acid sequence set forth in FIG. 1 having various portions of the C-terminus deleted were also prepared and tested for activity. Table 1, below, indicates the activity of the various polypeptides as well as their expression characteristics and their solubility. Expression was judged by SDS-polyacrylamide gel electrophoresis of total protein from the expression host. If the protein band corresponding to the neurotrophic factor was a major band in the total extract, expression was judged good. If the neurotrophic factor represented a minor protein band, expression was judged moderate. Little or no detectable protein band represented poor expression. The protein was judged to be soluble if greater than 90% of the protein remained in the aqueous phase following lysis by freeze/thawing.

TABLE 1

| Neurotrophic Factor | Activity (%) | Expression | Solubility |
|---|---|---|---|
| NF(1-190) | 100 | Good | Sol. |
| NF(1-180) | 50–100 | Good | Sol. |
| NF(1-178) | 50–100 | Good | Insol. |
| NF(1-176) | 10 | Good | Insol. |
| NF(1-174) | 10 | Good | Insol. |
| NF(1-172) | 10 | Good | Insol. |
| NF(21-180) | 10 | Good | Insol. |
| Controls | | | |
| NF(1-170) | None | Good | Insol. |
| NF(1-160) | None | Good | Insol. |

Example 6

Determination of Homogeneity

To evaluate the homogeneity of reverse phase-HPLC purified NF(1–180), the protein was subjected to electrospray mass spectroscopy. The protein gave a strong positive ion electrospray-MS spectrum with a single component having a molecular mass of 20,608±2. The excellent correlation of this calculated mass with the expected mass of 20,608.6 indicates that the protein has a C-terminus at Ser (amino acid No. 180). The lack of any significant components with alternate masses indicates that the sample is homogeneous.

Homogeneity was also evaluated by anion-exchange HPLC (Altex, DEAE column). The protein eluted as a single peak at 250–300 mM NaCl in 10 mM Tris, pH 8.0. By comparison, C-terminally heterogeneous samples of CNTF show multiple peaks during this analytic step.

Homogeneity was also demonstrated by tryptic digest of the protein. A tryptic map of the protein identified a single C-terminal tripeptide with the sequence Phe-Ile-Ser. No other terminal peptides were identified.

We claim:

1. A recombinant DNA sequence encoding a neurotrophic factor which can be expressed as an homogeneous polypeptide, said polypeptide having the amino acid sequence of residues No. m through n of FIG. 1 (SEQ ID NO. 002), wherein m is an integer from 1 to 21 and n is an integer from 180 to 192.

Figure 2:
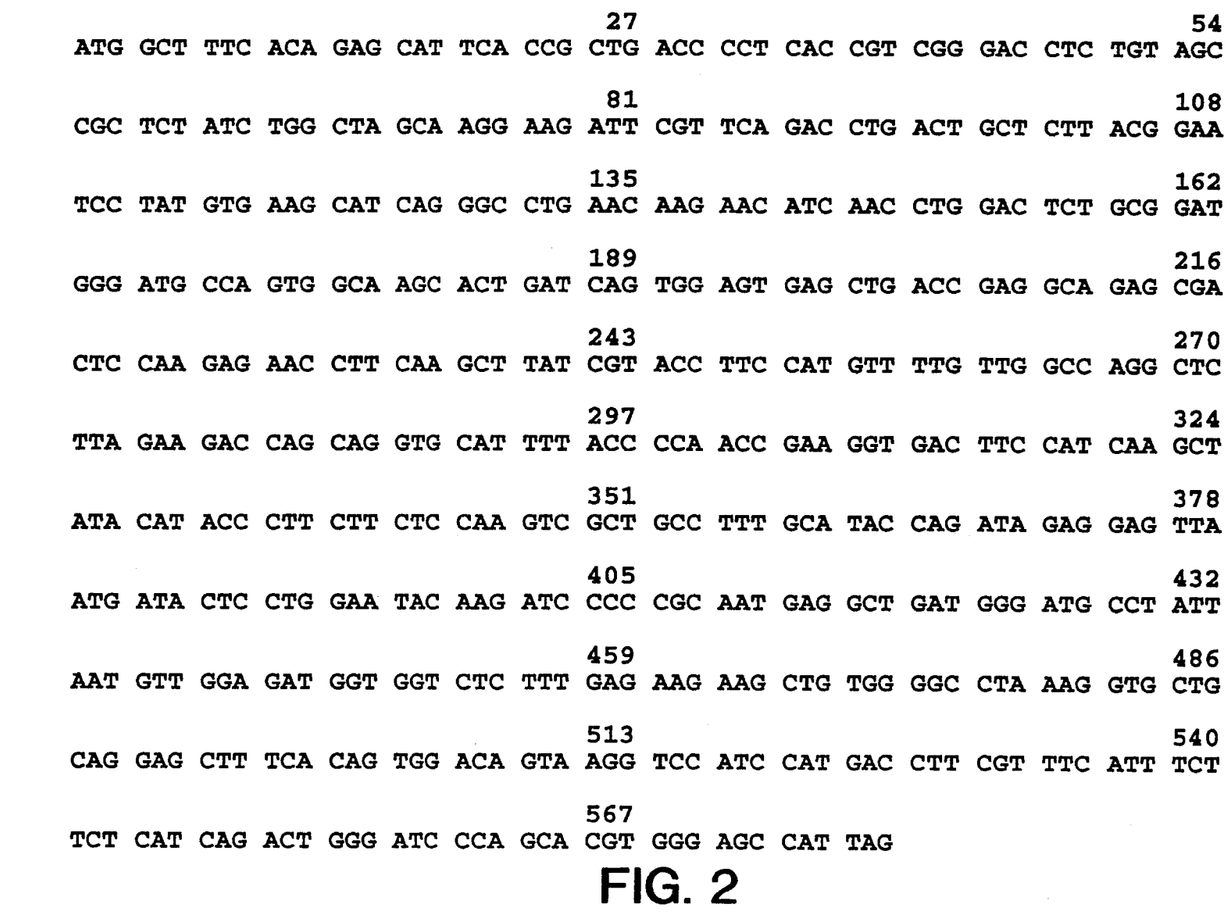
FIG. 2 represents a nucleotide sequence encoding the amino acid sequence of FIG. 1.
Figure 3:
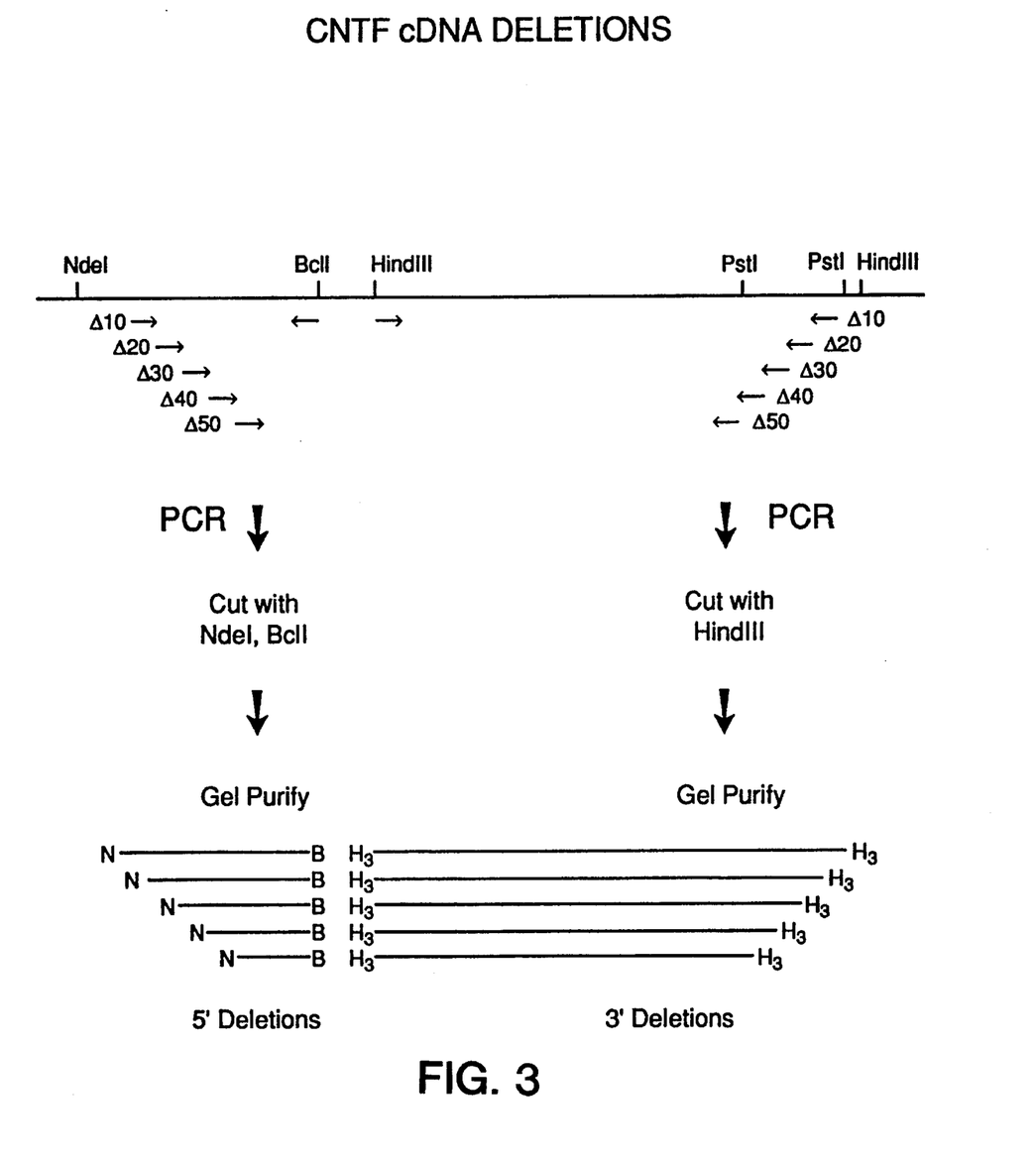

2. The recombinant DNA sequence of claim 1, containing the sequence of nucleotides No. 1–540 of FIG. 2 (SEQ ID NO. 001).

3. The recombinant DNA sequence of claim 1, containing the sequence of nucleotides No. 1–570 of FIG. 2 (SEQ ID NO. 001).

4. The recombinant DNA sequence of claim 1 containing the sequence of nucleotides No. 61–540 of FIG. 2 (SEQ ID NO. 001).

5. A recombinant DNA sequence of claim 1, wherein the coding sequence for the neurotrophic factor is operably linked to control elements capable of directing expression in a host cell, said recombinant DNA sequence being replicable in the host cell.

6. A recombinant DNA sequence of claim 5, wherein the coding sequence for the neurotrophic factor encodes the polypeptide having the amino acid sequence of amino acids no. 1–190 of FIG. 1 (SEQ ID NO. 002).

7. A recombinant DNA sequence of claim 5, wherein the coding sequence for the neurotrophic factor encodes a polypeptide having the amino acid sequence of amino acids No. 21–180 of FIG. 1 (SEQ ID NO. 002).

8. A method for producing isolated homogeneous neurotrophic factor which comprises:

(a) expressing the DNA sequence of claim 1 encoding a neurotrophic factor in a bacterial host cell;

(b) lysing the host cell and applying the lysate to an immobilized material capable of binding the neurotrophic factor through hydrophobic interaction;

(c) eluting a fraction containing the neurotrophic factor from the immobilized material and contacting said fraction with an immobilized metal ion capable of forming a chelate complex with the neurotrophic factor;

(d) eluting a fraction containing the neurotrophic factor from the immobilized metal ion and applying said fraction to a reverse phase HPLC column; and (e) eluting from the reverse phase HPLC column a fraction containing isolated homogeneous neurotrophic factor.

9. A method of claim 8, wherein step (b) comprises applying the neurotrophic factor-containing fraction to a phenyl-sepharose column.

10. The method of claim 8, wherein, step d further comprises subjecting the fraction containing the neurotrophic factor to size-exclusion chromatography before applying said fraction to a reverse phase HPLC column.

11. A recombinant DNA sequence encoding a neurotrophic factor which can be expressed as a homogeneous polypeptide, said polypeptide having the amino acid sequence of residues No. 1 through n of FIG. 1 (SEQ ID NO. 002), wherein n is an integer from 172 to 179.

12. The recombinant DNA sequence of claim 11 containing the sequence of nucleotides No. 1–534 of FIG. 2 (SEQ ID NO. 001).

13. A recombinant DNA sequence of claim 11, wherein n is an integer from 178 to 179.

14. A recombinant DNA sequence of claim 11, wherein the coding sequence for the neurotrophic factor is operably linked to control elements capable of directing expression in a host cell, said recombinant DNA sequence being replicable in the host cell.

15. A recombinant DNA sequence of claim 14, wherein the coding sequence for the neurotrophic factor encodes the polypeptide having the amino acid sequence of amino acids No. 1–178 of FIG. 1 (SEQ ID NO. 002).

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 579 base pairs
        ( B ) TYPE: nucleic acid
        ( C ) STRANDEDNESS: double
        ( D ) TOPOLOGY: linear     ( i i ) MOLECULE TYPE: cDNA     ( i x ) FEATURE:
        ( A ) NAME/KEY: CDS
        ( B ) LOCATION: 1..576

( x i ) SEQUENCE DESCRIPTION: SEQ ID NO:1:

```
ATG GCT TTC ACA GAG CAT TCA CCG CTG ACC CCT CAC CGT CGG GAC CTC    48
Met Ala Phe Thr Glu His Ser Pro Leu Thr Pro His Arg Arg Asp Leu
 1               5                  10                  15

TGT AGC CGC TCT ATC TGG CTA GCA AGG AAG ATT CGT TCA GAC CTG ACT    96
Cys Ser Arg Ser Ile Trp Leu Ala Arg Lys Ile Arg Ser Asp Leu Thr
             20                  25                  30

GCT CTT ACG GAA TCC TAT GTG AAG CAT CAG GGC CTG AAC AAG AAC ATC   144
Ala Leu Thr Glu Ser Tyr Val Lys His Gln Gly Leu Asn Lys Asn Ile
         35                  40                  45

AAC CTG GAC TCT GCG GAT GGG ATG CCA GTG GCA AGC ACT GAT CAG TGG   192
Asn Leu Asp Ser Ala Asp Gly Met Pro Val Ala Ser Thr Asp Gln Trp
     50                  55                  60

AGT GAG CTG ACC GAG GCA GAG CGA CTC CAA GAG AAC CTT CAA GCT TAT   240
Ser Glu Leu Thr Glu Ala Glu Arg Leu Gln Glu Asn Leu Gln Ala Tyr
 65                  70                  75                  80

CGT ACC TTC CAT GTT TTG TTG GCC AGG CTC TTA GAA GAC CAG CAG GTG   288
Arg Thr Phe His Val Leu Leu Ala Arg Leu Leu Glu Asp Gln Gln Val
                 85                  90                  95

CAT TTT ACC CCA ACC GAA GGT GAC TTC CAT CAA GCT ATA CAT ACC CTT   336
His Phe Thr Pro Thr Glu Gly Asp Phe His Gln Ala Ile His Thr Leu
                100                 105                 110

CTT CTC CAA GTC GCT GCC TTT GCA TAC CAG ATA GAG GAG TTA ATG ATA   384
Leu Leu Gln Val Ala Ala Phe Ala Tyr Gln Ile Glu Glu Leu Met Ile
            115                 120                 125

CTC CTG GAA TAC AAG ATC CCC CGC AAT GAG GCT GAT GGG ATG CCT ATT   432
Leu Leu Glu Tyr Lys Ile Pro Arg Asn Glu Ala Asp Gly Met Pro Ile
        130                 135                 140

AAT GTT GGA GAT GGT GGT CTC TTT GAG AAG AAG CTG TGG GGC CTA AAG   480
Asn Val Gly Asp Gly Gly Leu Phe Glu Lys Lys Leu Trp Gly Leu Lys
145                 150                 155                 160
```

|       |       |       |       |       |       |       |       |       |       |       |       |       |       |       |       |     |
|-------|-------|-------|-------|-------|-------|-------|-------|-------|-------|-------|-------|-------|-------|-------|-------|-----|
| GTG   | CTG   | CAG   | GAG   | CTT   | TCA   | CAG   | TGG   | ACA   | GTA   | AGG   | TCC   | ATC   | CAT   | GAC   | CTT   | 528 |
| Val   | Leu   | Gln   | Glu   | Leu   | Ser   | Gln   | Trp   | Thr   | Val   | Arg   | Ser   | Ile   | His   | Asp   | Leu   |     |
|       |       |       | 165   |       |       |       |       | 170   |       |       |       |       | 175   |       |       |     |
| CGT   | TTC   | ATT   | TCT   | TCT   | CAT   | CAG   | ACT   | GGG   | ATC   | CCA   | GCA   | CGT   | GGG   | AGC   | CAT   | 576 |
| Arg   | Phe   | Ile   | Ser   | Ser   | His   | Gln   | Thr   | Gly   | Ile   | Pro   | Ala   | Arg   | Gly   | Ser   | His   |     |
|       |       |       | 180   |       |       |       |       | 185   |       |       |       |       | 190   |       |       |     |
| TAG   |       |       |       |       |       |       |       |       |       |       |       |       |       |       |       | 579 |

( 2 ) INFORMATION FOR SEQ ID NO:2:

( i ) SEQUENCE CHARACTERISTICS:
        ( A ) LENGTH: 192 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Ala Phe Thr Glu His Ser Pro Leu Thr Pro His Arg Arg Asp Leu
 1           5                    10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
 65                 70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:3:

CCTTCAAGCT TATCGTACCT TCCATGTTTT GTTG        34

( 2 ) INFORMATION FOR SEQ ID NO:4:

( i ) SEQUENCE CHARACTERISTICS:
        ( A ) LENGTH: 38 base pairs
        ( B ) TYPE: nucleic acid
        ( C ) STRANDEDNESS: single (D) TOPOLOGY: linear (ii) MOLECULE TYPE: DNA (xi) SEQUENCE DESCRIPTION: SEQ ID NO:4:

CCAAGCTTCT AAGAAATGAA ACGAAGGTCA TGGATGGA  38

(2) INFORMATION FOR SEQ ID NO:5:

(i) SEQUENCE CHARACTERISTICS:
 (A) LENGTH: 47 base pairs
 (B) TYPE: nucleic acid
 (C) STRANDEDNESS: single
 (D) TOPOLOGY: linear (ii) MOLECULE TYPE: DNA (xi) SEQUENCE DESCRIPTION: SEQ ID NO:5:

ACGTAAAAAG GGTATCACAT ATGATCTGGC TAGCAAGGAA GATTCGT  47

(2) INFORMATION FOR SEQ ID NO:6:

(i) SEQUENCE CHARACTERISTICS:
 (A) LENGTH: 27 base pairs
 (B) TYPE: nucleic acid
 (C) STRANDEDNESS: single
 (D) TOPOLOGY: linear (ii) MOLECULE TYPE: DNA (xi) SEQUENCE DESCRIPTION: SEQ ID NO:6:

GGTTCTCTTG GAGTCGCTCT GCCTCGG  27